United States Patent [19]

Andresen

[11] 4,397,560
[45] Aug. 9, 1983

[54] PHOTOMETER WITH MICROTRAY WELL POSITION INDICATOR

[75] Inventor: Richard P. Andresen, Shelburne, Vt.

[73] Assignee: Bio-Tek Instruments, Inc., Burlington, Vt.

[21] Appl. No.: 256,648

[22] Filed: Apr. 23, 1981

[51] Int. Cl.³ .................................. G01B 7/03
[52] U.S. Cl. .......................... 356/440; 33/1 M; 340/870.31
[58] Field of Search ............ 340/870.31, 870.32, 340/870.33, 870.40, 870.41; 33/1 M; 356/440, 442, 443, 444

[56] References Cited

U.S. PATENT DOCUMENTS 3,024,396  3/1962  Peckjian ........................... 33/1 M
3,505,869  4/1970  Crawford ..................... 340/870.31
3,956,588  5/1976  Whetstone et al. ............... 33/1 M Primary Examiner—R. A. Rosenberger

[57] ABSTRACT

A photometer for sensing the optical density of a plurality of liquids located in a microtray provided with a rectilinear array of wells is provided with a detent device for locating each well in alignment with the photodetector and a plurality of magnets associated with the microtray and a plurality of magnet sensors associated with the photodetector for providing signals indicative of the specific well in alignment with the photodetector. A carrier having two bar magnets disposed at right angles to each is provided for supporting the microtray with the two bar magnets disposed parallel to adjacent sides of the microtray. Two linear arrays of equally spaced magnet sensors extend outwardly from the location of the photodetector at right angles to each other and at right angles to the bar magnets, respectively.

9 Claims, 3 Drawing Figures

PHOTOMETER WITH MICROTRAY WELL POSITION INDICATOR

BACKGROUND OF THE INVENTION

The present invention is directed to a photometer for sensing the optical density of liquids carried in a plurality of wells in a specimen tray in rows and columns, and more specifically, to an automatic device for indicating by row and column the particular well disposed in operative position relative to the photometer.

Conventional photometers are known for determining the optical density of a plurality of liquids contained in the individual wells of a microtray. The microtray is freely movable over a flat surface having an aperture therein. A light source or photocell is positioned above the aperture with the other being located in alignment therewith beneath the aperture so that the light will pass through the liquid in a well when the well is moved into alignment with the aperture. The rows of wells in the specimen tray are generally designated by letters while the columns are designated by numbers, so that a particular well would be identified by a letter and number combination. While some tactile device such as detent means are associated with the microtray and photometer to insure the exact positioning of each well in alignment with the optical system of the photometer, the particular wells undergoing examination can only be identified by careful visual scrutiny in tracing the row and column to the edge of the tray to determine the identifying letter and number. Such a procedure frequently leads to error in the identification of a particular well and the recording of the well identification and the value of the optical density for the particular well is a time consuming and tedious process which lends itself to the commission of additional errors.

SUMMARY OF THE INVENTION

The present provides a new and improved photometer adapted to save time and eliminate errors in the measurement of the optical density of a liquid in a well of a microtray and the designation of the particular well by row and column. The measurement of the optical density and the designation of the well by row and column is displayed substantially instantaneously on relatively large clearly readable LED digital display devices associated with the photometer. An optional printer read-out can be provided for the photometer to provide a permanent record of a well designation and the optical density of the liquid in said well.

The present invention provides a new and improved photometer having means for determining and displaying the rectangular grid coordinates of any selected sample well of a microtray containing a rectangular array of sample wells. Detent means are provided in association with the photometer which interact with the selected well to accurately locate the well relative to the photometer. The microtray is supported by a carrier which is moved over a flat support surface by hand from well to well. The detent means leaves the carrier free to rotate about the selected well and the invention tolerates sufficient rotation to enable a person to conveniently move the carrier without need of maintaining rigid alignment of the carrier with the edges of the flat surface. Magnetic means associated with the movable carrier and two sensor arrays located beneath the flat surface provide signals which are transmitted to encoding circuitry for an alpha-numeric display device which will display the identity of the well engaged by the detent means by row and column.

The foregoing objects, features and advantages of the present invention will be apparent from the following more particular description of a preferred embodiment of the invention as illustrated in the accompanying drawings.

DETAILED DESCRIPTION OF THE INVENTION

Figure 1:
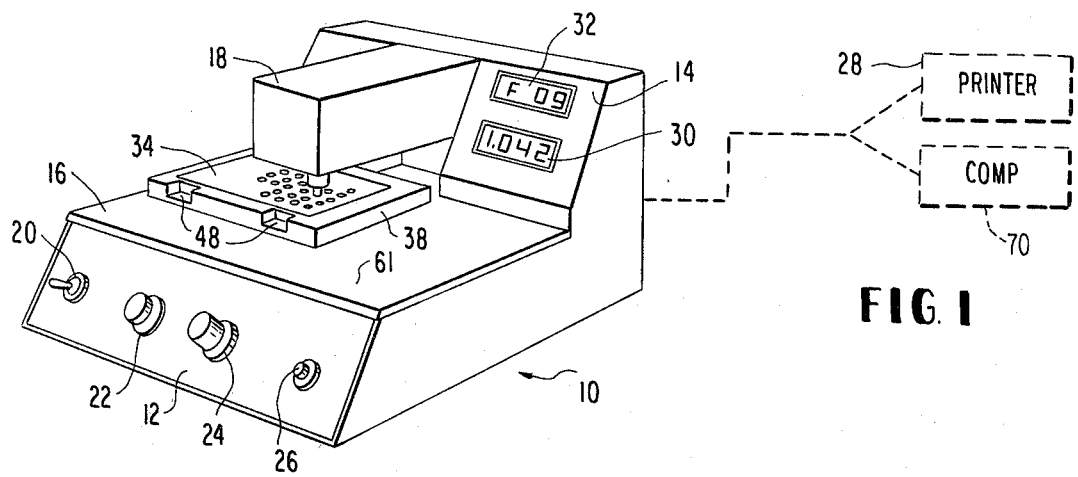
FIG. 1 is a perspective view of the photometer according to the present invention with LED digital displays for displaying the optical density and identification of a liquid filled well.

The photometer 10 of the present invention shown in FIG. 1 includes a control panel 12, a display panel 14, a carrier support surface 16 and a cantilevered arm 18 for supporting either the light source or photodetector in spaced relation above the support surface 16 at approximately the center thereof. The control panel 12 carries an on/off switch 20, an audible timer 22 which will emit an audible signal at chosen intervals to aid in adding substrate or taking timed readings, a zero setting device 24 for the photometer and a remote print button 26 for controlling the operation of the printer 28 which will record the reading for a particular well and the identification thereof. The display panel 14 includes an LED digital display 30 for the observance values and an LED digital display 32 for the well identification.

Figure 3:
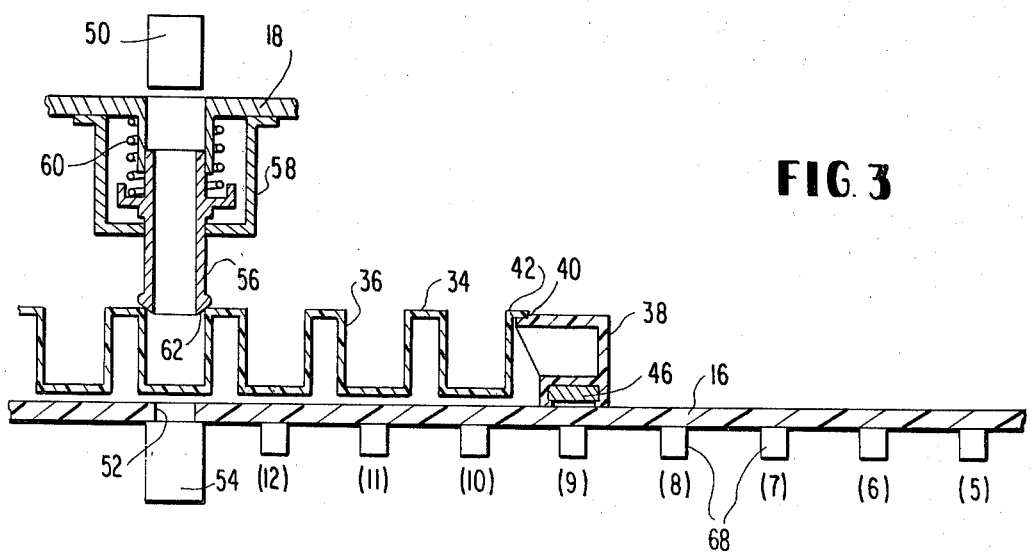
FIG. 3 is a vertical view of the photometer and carrier taken along a row of wells vertically aligned with the column sensors.

A microtray 34 is comprised of clear plastic material having a plurality of wells 36 formed therein and arranged in rows and columns for holding a plurality of liquids. Such microtrays 34 are fairly conventional in the industry and are generally provided with alphabet designations for the rows of wells and numerical designations for the columns of wells molded integrally therewith. Conventional microtrays 34 are generally provided with 96 wells in eight rows of twelve wells each. The microtray 34 is carried by a rectilinear carrier frame 38 which is adapted to rest freely on the support surface 16 of the photometer. The frame 38 has an open center in which the microtray 34 may be supported by any suitable means. In the embodiment shown in FIG. 3, the upper surface of the frame is provided with a recess 40 about the inner peripheral edge thereof for receiving the peripheral flange 42 of the microtray so that the wells will be supported in closely spaced apart relation to the support surface 16. For those microtrays having peripheral skirt portions depending downwardly from the flange 42 to a point just below the bottom of the wells, a modified frame construction would be provided for supporting such a microtray with the wells in approximately the same position relative to the support surface 16. The side members of the frame 38 are substantially hollow and two of the side members are so constructed and arranged to support elongated bar magnets 44 and 46 therein in closely spaced apart relation to the support surface 16. The two bar magnets 44 and 46 are disposed at right angles to each other and aligned with the axes of the rectangular array of wells in the microtray 34. The magnets are magnetized in a direction vertical to the flat surface upon which the frame 38 slides and each magnet is as long as the side of the array adjacent thereto. As shown in FIG. 3, the magnet 46 is supported along its longitudinal edges by flanges on the frame 38 so that most of the surface of the magnet will be exposed to the support surface 16. The magnet 44 can be mounted in a similar manner. The carrier frame 38 as shown in FIG. 1 is further provided with recesses 48 in at least one edge to facilitate removal of the microtray 34 from the carrier frame 38.

Figure 2:
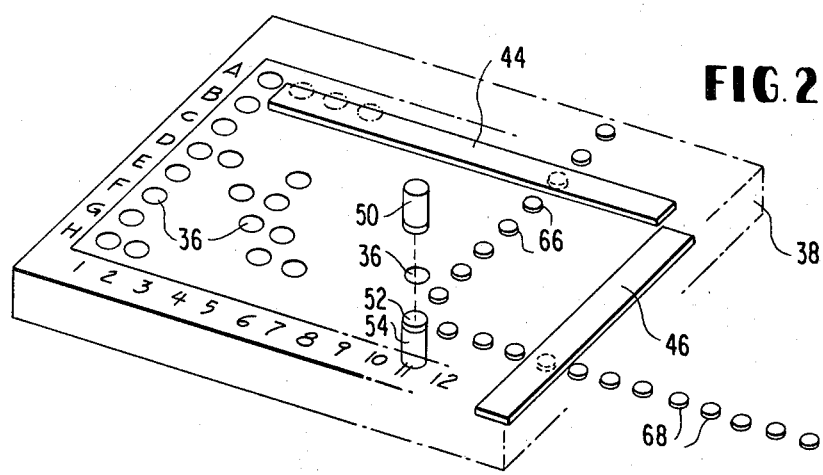
FIG. 2 is a schematic view of the magnets associated with the carrier and the sensors associated with the photometer to provide well identification signals.

Since photometers ae generally well known, the details of the photometer according to the present invention and the circuitry for providing the reading on the digital display 30 are not disclosed in detail. However, as best seen in FIGS. 2 and 3, the light source 50 is located in the cantilevered arm 18 above an aperture 52 in the support surface 16 and a photodetector 54 such as a silicon photodiode is located below the aperture 52 in alignment with the light source 50. A light tube 56 is slidably supported for reciprocating movement in a housing 58 depending from the under side of the cantilevered arm 18 with the hollow cylindrical light tube 56 being in alignment with the light source 50, aperture 52 and photodetector 54. Spring means 60 are located within the housing 58 for lightly biasing the tube 56 downwardly into engagement with the upper surface of the microtray 34. An annular beveled edge 62 is provided about the lower extremity of the tube 56 and the tube 56 is so dimensioned that the beveled surface is adapted to extend partially within a particular well and act as a locating detent. When the carrier frame 38 is moved over the flat support surface 16 by hand from well to well, a particular well will be accurately located by the beveled surface or detent 62 acting on the selected well 36. The detent 62 leaves the carrier 38 free to rotate about the selected well and the invention tolerates sufficient rotation to enable a person to conveniently move the carrier frame 38 without needing to maintain rigid alignment of the carrier frame 38 with the edges of the flat surface. Guide lines 61 may be printed or inscribed on the support surface 16 to visually assist in the guidance of the frame 38. The arrangement according to present invention tolerates approximately plus or minus seven degrees (±7°) of rotation. The detent 62 provides tactile feedback when a well is detected to assist the operator in properly locating the well in alignment with the photodetector system.

Underneath or imbedded in the panel having the flat support surface 16 are two linear arrays of spaced Hall effect magnetic sensors which detect the location of the bar magnets 44 and 46. The first sensor array is comprised of a line of eight sensors 66 and the second sensor array is a line of twelve sensors 68 with the sensors in each row being spaced the same distance as the wells in the microtray 34. Each sensor array is located at right angles to its corresponding bar magnet so that the corresponding bar magnet will only activate one sensor at a time. The length of the corresponding magnet in the carrier allows for motion along the axis not detected by the sensor array. Such a scheme allows detection coordinates of an nxm well array using only n plus m sensors. Furthermore, the width of each bar magnet is made approximately equal to the well spacing. The width of the magnet is normally centered over the sensor to be activated but as the carrier rotates from perfect rectangular alignment with the sensor array, the width moves off center. However, the magnetic field is wide enough due to the width to maintain the sensor activated for reasonable amounts of rotation, as indicated above.

The particular well 36 in alignment with the photometer is identified in the LED display 32 adjacent the optical reading for that particular well which is in the LED display 30. In the example shown in FIG. 2, the well F-09 is located in alignment with the aperture 52 in the support surface 16. Since there are eight rows of wells, eight sensors 66 are provided in the sensor array which will extend substantially perpendicular to the row magnet 44. Since there are twelve columns of wells, twelve sensors 68 are provided in the sensor array which will extend substantially perpendicular to the column magnet 46. The aperture 52 is disposed at the point of intersection of the two arrays which are disposed perpendicular to each other. With microtray 34 positioned as shown in FIG. 2, the row magnet 44 will be positioned over the sixth sensor 66 from the aperture 52 and the encoding circuitry will cause the letter F to be displayed in the LED digital display 32. The ninth sensor 68 from the right hand end of the array shown in FIG. 2 will be aligned with the column magnet 46 and the encoding circuitry will cause the digits 09 to be displayed adjacent the letter F in the LED digital display 32.

As mentioned previously, a suitable electrical connection can be made from the encoding circuitry directly to a printer 28 so as to obtain a permanent record of the optical reading for each well in a microtray. Likewise, the encoding circuitry could be connected directly to a computer 70 for comparison, storage or any other desired purpose.

The specific type of sensor used may vary as well as the manner in which the sensors are mounted relative to the support surface 16. Also, the manner in which the magnets are mounted in the frame can also vary. The magnets could be located in the other side of the frame 38 and the same results could be obtained with minor changes in the encoding circuitry.

While the well position indicator has been disclosed in combination with a photometer, it is also conceivable that the foregoing system of magnets and sensors could be utilized for identifying any well or point in a rectilinear array of equally spaced wells or points on one member relative to a fixed point on another member which is movable relative thereto.

While the invention has been particularly shown and described with reference to a preferred embodiment thereof, it will be understood by those in the art that various changes in form and details may be made therein without departing from the spirit and scope of the invention.

What is claimed is:
1. In a photometer of the type having a flat support surface with a single substantially centrally located aperture therethrough, photodetector means for detectin and displaying optical density of different liquids disposed in a plurality of equally spaced apart wells arranged in rows and columns in a microtray adapted to be freely movable over said surface for positioning different wells in alignment with said aperture and said photodetector means and locating means for locating each well in properly aligned relation, the improvement comprising:

carrier means having a rectilinear central opening for receiving and supporting a microtray having a plurality of equally spaced wells in a plurality of rows and columns formed therein, magnetic means supported by said carrier means, and, magnetic sensor means associated with said surface in a predetermined pattern relative to said aperture for generating signals capable of identifying a specific well by row and column in alignment with said aperture by the superimposed relation of said magnetic means relative to said magnetic sensor means.

2. A photometer as set forth in claim 1, wherein said magnetic means is comprised of two elongated bar magnets disposed at right angles to each other and extending along substantially the entire length of two sides of the rectilinear central opening in said carrier means.

3. A photometer as set forth in claim 2, wherein said pattern of magnetic sensors is comprised of two linear arrays with the sensors in each array being equally spaced from each other a distance equal to the spacing between the wells of said microtray, one linear array being perpendicular to the other linear array with the aperture in said surface being located at the point of intersection between said two linear arrays and the number of sensors in the linear array adapted to be substantially parallel to the columns of wells being equal to the number of wells in a column while the number of wells in the other array which is adapted to be substantially parallel to a row of wells is equal to the number of wells in a row.

4. A photometer as set forth in claim 1, further comprising digital display means adapted to identify a particular well by an alphanumerical display in response to activation of said sensor means by said magnet means.

5. A photometer as set forth in claim 4, further comprising printing means adapted to be connected to said photometer for printing the identification of each well and the associated optical values sensed by said photodetector means with respect to each well.

6. A position indicator for identifying the location of a first fixed point on a first member relative to a plurality of equally spaced second points in a pattern of rows and columns on a second member movable relative to said first member, comprising:

means for locating one of said second points in superimposed relation to said first fixed point, magnet means operatively associated with said second member, and magnet sensor means operably associated with said first member in a predetermined pattern relative to said first fixed point for generating signals capable of identifying a specific second point by row and column in alignment with said first fixed point by the superimposed relation of said magnet means relative to said magnet sensor means.

7. A position indicator as set forth in claim 6, wherein said magnet means is comprised of two elongated bar magnets carried by said second member perpendicular to each other and extending along two adjacent sides of said pattern of second points.

8. A position indicator as set forth in claim 7, wherein said magnet sensor means are comprised of a plurality of magnetic sensors disposed in a first linear array and a plurality of second sensors disposed in a second linear array, said first and second linear arrays being disposed perpendicular to each other and intersecting at said first fixed point and adapted to be disposed substantially perpendicular to a respective bar magnet on said second member.

9. A position indicator as set forth in claim 8, further comprising display means responsive to magnetic sensors activated by a superimposed magnet for providing an alphanumeric display indicative of the second point in alignment with said first fixed point.

* * * * *